US011160231B2

(12) United States Patent
Sha

(10) Patent No.: US 11,160,231 B2
(45) Date of Patent: Nov. 2, 2021

(54) RICE CULTIVAR 'CLM04'

(71) Applicant: THE BOARD OF TRUSTEES OF THE UNIVERSITY OF ARKANSAS, Little Rock, AR (US)

(72) Inventor: Xueyan Sha, Stuttgart, AR (US)

(73) Assignee: THE BOARD OF TRUSTEES OF THE UNIVERSITY OF ARKANSAS, Little Rock, AR (US)

( * ) Notice: Subject to any disclaimer, the term of this patent is extended or adjusted under 35 U.S.C. 154(b) by 0 days.

(21) Appl. No.: 16/656,119

(22) Filed: Oct. 17, 2019

(65) Prior Publication Data
US 2021/0112746 A1 Apr. 22, 2021

(51) Int. Cl.
*A01H 5/10* (2018.01)
*A01H 6/46* (2018.01)

(52) U.S. Cl.
CPC .............. *A01H 6/4636* (2018.05); *A01H 5/10* (2013.01)

(58) Field of Classification Search
None
See application file for complete search history.

(56) References Cited

U.S. PATENT DOCUMENTS 7,351,891 B2 * 4/2008 Sarreal .................... A01H 5/10
435/410

OTHER PUBLICATIONS

Bairu et al. Plant Growth Regul (2011)63:147-173.*
Adair C.R. et al. 1972. Rice in the United States: Varieties and Production. USDA Handbook No. 289 (Rev.), 124 pp.
Atkins J.G. et al. 1967. An International Set of Rice Varieties for Differentiating Race of Pyricularia Oryzae. Phytopath. 57:297-301.
International Rice Research Institute. IBPGR-IRRI Rice Advisory Committee. 1980. Descriptors for Rice *Oryzae sativa* L. 21 pp.
Ling K. C. et al, 1969. Standardization of the International Race Numbers of Pyricularia Oryzae. Phytopath. 59:339-342.
Linscombe, S.D., et al. 1993. Registration of 'Bengal' rice. Crop Science 33:645-646.
Sha, X. et al. 2006 Registration of 'Jupiter' rice. Crop Science 46:1811-1812.
Sha, X., et al. 2007. Field evaluation of Imidazolinone-tolerant Clearfield rice (*Oryza sativa*) at nine Louisiana locations. Crop Science 47:1177-1185.
Sha, X., et al. 2010. Registration of 'Neptune' southern medium-grain rice. Journal of Plant Registrations 4:179-182.
Webb B.D. et al. 1985. Utilization Characteristics and Qualities of United States Rice. In Proceedings on Rice Grain Quality and Marketing. International Rice Research Institute (IRRI), Los Branos, Philippines. p. 25-35.

* cited by examiner

*Primary Examiner* — Medina A Ibrahim
(74) *Attorney, Agent, or Firm* — Quarles & Brady LLP

(57) ABSTRACT

A rice cultivar designated CLM04 is disclosed herein. The present invention provides seeds, plants, and plant parts derived from rice cultivar CLM04. Further, it provides methods for producing a rice plant by crossing CLM04 with itself or another rice variety and methods for combating undesired vegetation by contacting the disclosed rice seeds with an AHAS-inhibiting herbicide. The invention also encompasses any rice seeds, plants, and plant parts produced by the methods disclosed herein, including those in which additional traits have been transferred into CLM04 through the introduction of a transgene or by breeding CLM04 with another rice cultivar.

30 Claims, No Drawings

RICE CULTIVAR 'CLM04'

BACKGROUND OF THE INVENTION

The present invention relates to a new and distinctive rice cultivar, designated CLM04. Rice is an ancient agricultural crop and is today one of the principal food crops of the world. There are two cultivated species of rice: *Oryza sativa* L., the Asian rice, and *O. glaberrima* Steud., the African rice. *O. sativa* L. constitutes virtually all of the world's cultivated rice and is the species grown in the United States. Three major rice producing regions exist in the United States: the Mississippi Delta (Arkansas, Mississippi, northeast Louisiana, southeast Missouri), the Gulf Coast (southwest Louisiana, southeast Texas), and the Central Valleys of California.

Rice is a semi-aquatic crop that benefits from flooded soil conditions during part or all of the growing season. In the United States, rice is grown on flooded soils to optimize grain yields. Heavy clay soils or silt loam soils with hard pan layers about 30 cm below the surface are preferred rice-producing soils because they minimize water losses from soil percolation. Rice production in the United States can be broadly categorized as either dry-seeded or water-seeded. In the dry-seeded system, rice is sown into a well-prepared seed bed with a grain drill or by broadcasting the seed and incorporating it with a disk or harrow. Moisture for seed germination is provided by irrigation or rainfall. Alternatively, the seed may be broadcast by airplane into a flooded field, which is promptly drained following seeding. With the dry-seeded system, when the plants have reached sufficient size (four- to five-leaf stage), a shallow permanent flood of water, 5 to 16 cm deep, is applied to the field for the remainder of the crop season.

In the water-seeded system, rice seed is soaked for 12 to 36 hours to initiate germination, and the seed is broadcast by airplane into a flooded field. The seedlings emerge through a shallow flood, or the water may be drained from the field for a short period of time to enhance seedling establishment. A shallow flood is maintained until the rice approaches maturity. For both the dry-seeded and water-seeded production systems, the fields are drained when the crop is mature, and the rice is harvested 2 to 3 weeks later with large combines. In rice breeding programs, breeders typically employ the production systems predominant in their respective region. Thus, a drill-seeded breeding nursery is used by breeders in a region where rice is drill-seeded and a water-seeded nursery is used in regions where water-seeding is prominent.

Rice in the United States is classified into three primary market types by grain size, shape, and chemical composition of the endosperm: long-grain, medium-grain and short-grain. Typical U.S. long-grain cultivars cook dry and fluffy when steamed or boiled, whereas medium- and short-grain cultivars cook moist and sticky. In the southern states, long-grain cultivars have traditionally been grown and generally receive higher market prices.

Rice, *Oryza sativa* L., is an important and valuable field crop. A continuing goal of plant breeders is to produce stable, high yielding rice cultivars that are agronomically sound. To accomplish this goal, rice plants with traits that result in superior cultivars must be developed.

SUMMARY OF THE INVENTION

The present invention provides a novel rice cultivar designated CLM04. The invention encompasses the seeds, plants, and plant parts of rice cultivar CLM04, as well as plants with essentially all of the physiological and morphological characteristics of CLM04.

In another aspect, the present invention provides seeds of rice cultivar CLM04 that are treated with an acetohydroxy-acid synthase (AHAS)-inhibiting herbicide. Further, this invention provides methods for combating undesired vegetation by contacting the disclosed rice seeds with an AHAS-inhibiting herbicide.

This invention also provides methods for producing a rice plant by planting a plurality of seeds or by crossing rice CLM04 with itself or another rice line. Any plant breeding methods using rice variety CLM04 are part of this invention, including selfing, backcrosses, hybrid production, and crosses to populations. All plants and seeds produced using rice variety CLM04 as a parent are within the scope of this invention, including gene-converted plants of CLM04. Methods for introducing a gene into CLM04, either through traditional breeding or transformation, are provided herein.

In still another aspect, the present invention provides regenerable cells for use in tissue culture of rice plant CLM04, as well as rice plants regenerated from these tissue cultures.

Definitions

To provide a clear and consistent understanding of the specification and claims, the following definitions are provided:

Abiotic stress. Stress caused by any non-living chemical or physical factors in the environment. Examples of abiotic stress include, but are not limited to, drought, flooding, salinity, temperature, and climate change.

Allele. One of two or more alternative forms of a gene, all of which relate to a single trait or characteristic. In a diploid cell or organism, two alleles of a given gene occupy corresponding loci on a pair of homologous chromosomes.

Apparent amylose content. The amount of starch in the endosperm of milled rice that is amylose, provided in g/kg herein. Amylose content varies depending on the growth environment of the rice. It is an important grain characteristic used to describe cooking behavior.

Backcrossing. A process in which a breeder repeatedly crosses hybrid progeny back to a parental line. For example, a first generation (F1) hybrid may be crossed with one of the parental lines used to produce the F1 hybrids.

Breeding. The genetic manipulation of living organisms.

Cell. As used herein, this term includes isolated cells, cells grown in tissue culture, and cells that comprise a plant or plant part.

Cultivar. Used interchangeably with "variety". Refers to plants that are defined by the expression of the characteristics resulting from a given genotype or combination of genotypes, distinguished from any other plant grouping by the expression of at least one characteristic.

Days to 50% heading. The average number of days from emergence to the day when 50% of all panicles are exerted at least partially through the leaf sheath. A measure of maturity.

Embryo. The plant embryo is the part of a seed or bud that contains the earliest forms of the new plant's roots, stem and leaves.

Essentially all of the physiological and morphological characteristics. A plant having "essentially all the physiological and morphological characteristics" of the cultivar exhibits the characteristics of the cultivar with the exception of any characteristics derived from a converted gene.

F #. Denotes a filial generation, wherein the # is the generation number. For example, F1 is the first filial generation.

Gene. Refers to a unit of inheritance corresponding to a distinct sequence of DNA or RNA nucleotides that form part of a chromosome. A gene may encode a polypeptide or a nucleic acid molecule that has a function in a cell or organism.

Gene-converted. Describes a plant wherein essentially all of the desired morphological and physiological characteristics of a parental variety are maintained with the exception of a single trait that was transferred into the variety via backcrossing or genetic engineering.

Genotype. Refers to the genetic constitution of a cell or organism.

Grain yield. Measured in pounds per acre at 12.0% moisture content. The grain yield of rice is determined by the number of panicles per unit area, the number of fertile florets per panicle, and the grain weight per floret.

Haploid. A cell or organism having a single set of unpaired chromosomes.

Harvest moisture. The percent moisture content of the grain when harvested.

Head rice. Kernels of milled rice in which greater than ¾ of the kernel is unbroken.

Herbicide resistant. Describes a plant that that is tolerant or resistant to an herbicide at a level that would normally kill or inhibit the growth of a normal or wild-type rice plant.

Hybrid. Refers to the offspring or progeny of genetically dissimilar plant parents or stock produced as the result of controlled cross-pollination as opposed to a non-hybrid seed produced as the result of natural pollination.

Kernal length (L). Length of a rice grain, measured in millimeters.

Kernal width (W). Width of a rice grain, measured in millimeters.

Length/width (L/W) ratio. Determined by dividing the average length (L) by the average width (W).

Lodging. The percentage of plant stems that are leaning or have fallen to the ground before harvest. Lodging is determined by visual scoring, in which crops are rated from 0% (all plants standing) to 100% (all plant in plot lying flat on the soil surface). Lodged plants are difficult to harvest and reduce yield and grain quality. Lodging resistance is also called "straw strength".

Milling yield. The total amount of milled rice (whole and broken kernels) recovered after milling (i.e., removal of hulls, bran, and germ). In contrast, head rice yield is the total amount of whole kernels recovered after milling. Both values are expressed as a weight percentage of the original paddy or rough rice sample that was milled. For example, for a sample of 100 grams of rough rice, a milling yield of 65/70 indicates that 65 grams of head rice and 70 grams of total milled rice were produced.

Pedigree. Refers to the lineage or genealogical descent of a plant.

Plant. As used herein, the term "plant" includes plant cells, plant protoplasts, and plant cell tissue cultures from which rice plants can be regenerated; plant calli, plant clumps and plant cells that are intact in plants; and parts of plants, such as embryos, pollen, ovules, flowers, glumes, panicles, leaves, stems, roots, root tips, anthers, and pistils.

Plant height. Measured in centimeters from the soil surface to the tip of the extended panicle at harvest.

Plant parts. Includes, without limitation, protoplasts, leaves, stems, roots, root tips, anthers, pistils, seed, grain, embryo, pollen, ovules, cotyledon, hypocotyl, pod, flower, shoot, tissue, petiole, cells, and meristematic cells.

Progeny. Includes an F1 rice plant produced from the cross of two rice plants, as well as plants produced from subsequent generational crosses (e.g., F2, F3, F4, F5, F6, F7, F8, F9, and F10) with the recurrent parental line.

Regeneration. Refers to the development of a plant from tissue culture.

Seeds. Includes seeds and plant propagules of all kinds including, but not limited to, true seeds, seed pieces, suckers, corms, bulbs, fruit, tubers, grains, cuttings, cut shoots and the like.

However, in preferred embodiments, it refers to true seeds.

Trait. Refers to an observable and/or measurable characteristic of an organism. For example, the present invention describes plants that have a trait that make them resistant to herbicides.

Transgenic. Describes an organism or cell that contains genetic material that has been artificially introduced.

Wild-type. When made in reference to a gene, "wild-type" refers to a functional gene common throughout a plant population and, thus, arbitrarily designated the "normal" or "wild-type" form of the gene.

DETAILED DESCRIPTION OF THE INVENTION

The present invention provides a novel rice cultivar designated CLM04. The invention encompasses both the seeds of this cultivar and plants grown from these seeds. The invention further encompasses any rice plant having essentially all of the physiological and morphological characteristics rice cultivar CLM04.

As used herein, the term plant includes plant cells, plant protoplasts, plant cell tissue cultures from which rice plants can be regenerated, plant calli, plant clumps and plant cells that are intact in plants or parts of plants, such as embryos, pollen, ovules, flowers, glumes, panicles, leaves, stems, roots, root tips, anthers, pistils, and the like.

Development and Characterization of CLM04

Rice cultivar CLM04 is a high yielding, early maturing, and short stature Clearfield® medium-grain rice (*Oryza sativa* L.) experimental line developed at the Rice Research and Extension Center (RREC), University of Arkansas Division of Agriculture in Stuttgart, Ark.

CLM04 was originally selected from the cross 13CRS187 with a pedigree of 'Neptune'//'Bengal'/'CL161'/3/'Jupiter' made at RREC in spring 2013. 'Neptune', 'Bengal', and 'Jupiter' are southern medium-grain rice varieties developed by Louisiana State University Agricultural Center's Rice Research Station (LSU-RRS) near Crowley, La. (Sha, et al, 2010, Linscombe et al, 1993; and Sha et al, 2006), while 'CL161' (Sha, et al., 2007) is the first imidazolinone-resistant CL long-grain rice variety developed by LSU-RRS. 'CLM04' initiated as a F4 bulk of a single progeny row 14P54617 at RREC in summer 2014. It was evaluated in the preliminary CL Stuttgart initial trial (CL SIT) in 2015 as entry 15CSIT474, and entered the Arkansas Rice Performance Trial (ARPT) and the Cooperative Uniform Regional Rice Nurseries (URRN) in 2016 with the experimental designation RU1601030. It was also evaluated in the Advanced/Elite Line Yield Trial (AYT) and the Medium-grain Producer Rice Evaluation Program (PREP-MG) trials in 2017 and 2018, as well as in the Advanced Clearfield Yield Trial and Producer Rice Evaluation Program (PREP) trials in 2018.

CLM04 appears to have an outstanding yield potential, good milling and grain quality, and good lodging and blast resistance compared with 'CL272', 'Jupiter', and 'Tita'n. In 43 statewide and regional trials during 2016-2018, the average grain yield at 120 g kg-1 moisture of 'CLM04' is 8,909 pounds/acre or 198 bushels/acre compared with 8,418 or 187 of 'CL272', 8,793 or 195 of 'Jupiter', and 9,007 or 200 of 'Titan', respectively. Average milling yields (g kg-1 whole milled kernels: g kg-1 total milled rice) at 23 state and regional tests from 2016-2018 were 601:680 for 'CLM04', 574:687 for 'CL272', 606:682 for 'Jupiter', and 584:690 for 'Titan', respectively. 'CLM04' has a semi-dwarf plant type and is moderately susceptible to lodging. It measured 106 cm in height in yield trials across Mid-South and is slightly taller than the 102 cm of 'CL272'. 'CLM04' has a similar maturity as 'CL272' and 'Jupiter'. The average number of days from emergence to 50% heading is 86 as compared with 85, 87, and 81 of 'CL272', 'Jupiter', and 'Titan', respectively.

'CLM04' has the typical medium-grain shape, and its kernels appear larger than those of 'CL272' and 'Jupiter' but slightly smaller than those of 'Titan'. According to the analyses conducted by Riceland Foods, Inc. (Stuttgart, Ark.) on 12 different sets of samples collected across Arkansas during 2016-2017, the average length and width (mm), length/width ratio, and kernel weight (mg) of milled whole kernels of 'CLM04' are 5.81, 2.64, 2.21, and 22.34 as compared with 5.80, 2.58, 2.25, and 22.04 for 'CL272', 5.72, 2.56, 2.24, and 21.38 for 'Jupiter', and 5.90, 2.60, 2.28, and 22.76 for 'Titan', respectively. Average chalkiness is 2.6% of 'CLM04', as compared with 3.1, 2.9, and 2.5 of 'CL272', 'Jupiter', and 'Titan', respectively. Average apparent amylose content of 'CLM04' is 166 g kg-1 compared with 139, 161, and 159 g kg-1 of 'CL272', 'Jupiter', and 'Titan', respectively. 'CLM04' has a low gelatinization temperature of 62.6° C., which is similar to that of 'Jupiter' (62.6° C.). These results indicate that 'CLM04' has typical U.S. medium-grain rice cooking characteristics.

Results from the artificially inoculated rice blast nursery for leaf blast (caused by *Pyricularia grisea* (Cooke) Sacc.) indicated that 'CLM04' is moderately susceptible with a rating of 5.5 on a disease scale of 0=immune, 9=highly susceptible, as compared with 5.3, 5.4, and 5.0 of 'CL272', 'Jupiter', and 'Titan', respectively. However, molecular marker works indicated that 'CLM04' possesses both blast resistant genes Pi-z and Pi-ks, in contrast to 'Jupiter's' single Pi-ks resistance gene. In greenhouse inoculation tests, 'CLM04' showed susceptibility to blast races IB-1, IB-17, IB-49, and IE-1K, but resistance to IG-1 and moderate resistance to IC-17, IE-1, and IH-1. Under natural infestation or inoculation tests, 'CLM04' appeared susceptible to sheath blight (caused by *Rhizoctonia solani* Kühn), bacterial panicle blight (caused by *Burkholderia glumae*), kernel smut (caused by *Neovossia horrida*), and false smut (caused by *Ustilaginoidea virens* (Cooke) Takah).

The leaves, lemma, and palea of 'CLM04' are glabrous. The spikelet is straw colored. The apiculus is purple at heading and the color fades as grains approach maturity. The grain is non-aromatic.

Variants observed and removed from three increase fields of 'CLM04' were primarily shorter and earlier. Other variants included any combination of the following: pubescent, later, taller, long-, short-, and intermediate grain types, gold or black hull, and sterile panicle. The total number of variants numbered less than 1 per 5000 plants. The cultivar has thus shown relative uniformity and stability as described in the following variety description information.

The above-mentioned characteristics of rice cultivar 'CLM04' are based primarily on data collected in Stuttgart, Ark. and are summarized in Table 1.

TABLE 1

VARIETY DESCRIPTION INFORMATION

Plant:

Grain type: Medium
Days to maturity (Seeding to 50% heading): 86
Plant height: 106 cm
Plant color (at booting): Green
Culm:

Angle (degrees from perpendicular after flowering): Erect (less than 30°)
Flag leaf (after heading):

Pubescence: Glabrous
Leaf angle (after heading): Intermediate
Blade color (at heading): Green
Panicle:

Length: 20.6 cm
Type: Intermediate
Exertion (near maturity): Well
Axis: Droopy
Shattering (at maturity): Low (1-5%)
Grain (spikelet):

Awns (after full heading): Absent
Apiculus color: Purple
Stigma color: White
Lemma and palea color (at maturity): Straw
Lemma and palea pubescence: Glabrous
Grain (seed):

Seed coat color: Light brown
Scent: Nonscented
Shape class (length/width ratio):

Paddy: Medium (2.3:1 to 3.3:1)
Brown: Medium (2.1:1 to 3.0:1)
Milled: Medium (2.0:1 to 2.9:1)
Size: 27.9 g/1000 seeds milled rice
Disease resistance:

Rice blast (*Pyricularia grisea* (Cooke) Sacc.): Moderately susceptible
Sheath blight (*Rhizoctonia solani* Kuhn): Susceptible
False smut (*Ustilaginoidea virens* (Cooke) Takah.): Susceptible
Bacterial panicle blight (*Burkholderia glumae* and *B. gladioli*): Susceptible In the following tables, the agronomic characteristics of rice cultivar CLM04 are compared to those of other rice Clearfield rice cultivars.

TABLE 2

Overall average grain yield (at 12% H$_2$O) and milling yields (% head and total rice) of CLM04 and check varieties, 2016-2018.

| Variety | Grain Yield (Bu/A) | Grain Yield (Lb/A) | Milling Yield (%) Head Rice | Milling Yield (%) Total Rice |
|---|---|---|---|---|
| CLM04 | 198 | 8,909 | 60.1 | 68.0 |
| CL272 | 187 | 8,418 | 57.4 | 68.7 |
| Jupiter | 195 | 8,793 | 60.6 | 68.2 |
| Titan | 200 | 9,007 | 58.4 | 69.0 |
| No. trials | 43 | 43 | 23 | 23 |

TABLE 3

Overall average days to 50% heading, height, and lodging incidence of CLM04 and check varieties, 2016-2018.

| Variety | Seedling vigor† | Days to 50% heading | Plant height (inch) | Lodging incidence (%) |
|---|---|---|---|---|
| CLM04 | 4.2 | 86 | 42 | 4 |
| CL272 | 3.1 | 85 | 40 | 1 |
| Jupiter | 3.8 | 87 | 38 | 4 |
| Titan | 3.3 | 81 | 39 | 2 |
| No. trials | 9 | 24 | 22 | 43 |

†Subjective rating 1-7, 1 = perfect stand and 7 = no stand.

TABLE 4

Average amylose content, gelatinization temperature, chalkiness, kernel dimension and weight of milled rice of CLM04 and check varieties analyzed by Riceland Foods, Inc. (Stuttgart, AR) on samples collected across Arkansas, 2016-2018.

| Variety | Amylose content (%) | Gel temperature (° C.) | Chalkiness (%) | Length (L) mm | Width (W) mm | L/W ratio | Kernel weight (mg) |
|---|---|---|---|---|---|---|---|
| CLM04 | 16.6 | 62.6 | 2.63 | 5.81 | 2.64 | 2.21 | 22.4 |
| CL272 | 13.9 | 63.6 | 3.12 | 5.80 | 2.58 | 2.25 | 22.0 |
| Jupiter | 16.1 | 62.6 | 2.88 | 5.72 | 2.56 | 2.24 | 21.4 |
| Titan | 15.9 | 63.7 | 2.49 | 5.90 | 2.60 | 2.28 | 22.8 |
| No. trials | 12 | 12 | 12 | 11 | 11 | 11 | 9 |

TABLE 5

Grain dimensions and weight of CLM04 and check varieties, Stuttgart, AR, 2018.

| Variety | Length (L) | Width (W) | Thickness | L/W Ratio | Weight |
|---|---|---|---|---|---|
|  | mm | | | | mg |
| Paddy Rice | | | | | |
| CLM04 | 8.11 | 3.26 | 2.15 | 2.49 | 27.94 |
| CL272 | 7.70 | 3.10 | 2.09 | 2.48 | 26.54 |
| Jupiter | 7.80 | 3.31 | 2.10 | 2.36 | 26.13 |
| Titan | 7.85 | 3.17 | 2.14 | 2.48 | 27.99 |
| Brown Rice | | | | | |
| CLM04 | 6.00 | 2.77 | 1.94 | 2.17 | 22.66 |
| CL272 | 6.14 | 2.81 | 1.88 | 2.19 | 23.17 |
| Jupiter | 5.70 | 2.80 | 1.94 | 2.04 | 21.87 |
| Titan | 6.00 | 2.85 | 1.97 | 2.11 | 23.19 |
| Milled Rice | | | | | |
| CLM04 | 5.50 | 2.64 | 1.85 | 2.08 | 20.77 |
| CL272 | 5.49 | 2.63 | 1.78 | 2.09 | 20.37 |
| Jupiter | 5.29 | 2.63 | 1.71 | 2.01 | 18.88 |
| Titan | 5.54 | 2.67 | 1.71 | 2.07 | 20.00 |

TABLE 6

Average rating (0-9, 0 = immune and 9 = maximum) of CLM04 and check varieties against sheath blight, leaf blast, rotten neck blast, and bacterial panicle blight under artificial inoculation, 2016-2018. (Dr. Don Groth, 2016-2018, personal communications; Scott Belmar, 2016-2018, personal communications).

| Variety | Sheath blight | Leaf blast | Rotten neck blight | Bacterial panicle blight |
|---|---|---|---|---|
| CLM04 | 6.1 | 5.5 | 2.6 | 2.3 |
| CL272 | 6.0 | 5.3 | 3.2 | 2.4 |
| Jupiter | 6.3 | 5.4 | 1.5 | 2.0 |
| Titan | 6.6 | 5.0 | 2.0 | 2.0 |
| No. trials | 5 | 2 | 5 | 3 |

TABLE 7

Disease reactions (measured by a 0-9 rating scale, 0 = immune and 9 = maximum) of CLM04 and check varieties inoculated with different races of blast pathogen (*Pyricularia oryzae*) in the greenhouse, Stuttgart, AR. 2016-2017. (Scott Belmar, 2016-2018, Personal communications).

| Variety | IB-1 | IB-17 | IB-49 | IC-17 | IE1-K | IE-1 | IG-1 | IH-1 |
|---|---|---|---|---|---|---|---|---|
| CLM04 | S† | S | S | MR | S | MR | R | MR |
| CL272 | S | S | S | R | MR | S | R | R |
| Jupiter | S | S | S | S | S | S | S | S |
| Titan | S | S | S | MR | S | S | R | R |
| No. trials | 2 | 1 | 2 | 2 | 2 | 2 | 1 | 1 |

TABLE 7-continued

Disease reactions (measured by a 0-9 rating scale, 0 = immune and 9 = maximum) of CLM04 and check varieties inoculated with different races of blast pathogen (*Pyricularia oryzae*) in the greenhouse, Stuttgart, AR. 2016-2017. (Scott Belmar, 2016-2018, Personal communications).

| Variety | IB-1 | IB-17 | IB-49 | IC-17 | IE1-K | IE-1 | IG-1 | IH-1 |
|---|---|---|---|---|---|---|---|---|

†Disease reaction, R = resistant, MR = moderate resistant, and S = susceptible.

TABLE 8

CLM04 reactions to diseases and lodging, determined based on observations of test plots across Arkansas. (Yeshi Wamishe, personal communication, 2018).

| Affliction | Rating |
|---|---|
| Sheath Blight | — |
| Blast | S |
| Straighthead | S |
| Bacterial Panicle Blight | VS |
| Narrow Brown Leaf Spot | — |
| Stem Rot | — |
| Kernel Smut | — |
| False Smut | S |
| Lodging | — |
| Black Sheath Rot | — |
| Sheath Spot | — |

Reaction:
R = Resistant;
MR = Moderately Resistant;
MS = Moderately Susceptible;
S = Susceptible;
VS = Very Susceptible Cells with no values indicate no definitive disease rating information is available at this time. In general, these ratings represent expected cultivar reactions to disease under conditions that most favor severe disease development.

TABLE 9

Average grain yield of CLM04 and check varieties by location in the Arkansas Rice Performance Trial (ARPT) across rice growing regions of Arkansas, 2016-2018. (Dr. Jarrod Hardke, personal communication, 2018).

| Variety | Grain yield (bushels/acre at 12% H$_2$O) | | | | | | |
|---|---|---|---|---|---|---|---|
| | Chicot† | Clay | NEC | NEREC | PTRS | RREC | Mean |
| CLM04 | 209 | 195 | 135 | 192 | 197 | 193 | 192 |
| CL272 | 180 | 207 | 152 | 179 | 185 | 178 | 184 |
| Jupiter | 201 | 194 | 132 | 202 | 172 | 204 | 190 |
| Titan | 192 | 208 | 155 | 191 | 178 | 215 | 194 |

†Test location: Chicot = Chicot Co., AR., Clay = Clay Co., AR., NEC = Newport Extension Center near Newport, AR., NEREC = Northeast Research and Extension Center at Keiser, AR., PTRS = Pine Tree Research Station near Colt, AR., and RREC = Rice Research and Extension Center near Stuttgart, AR. During 2016-2018, trials were conducted at all locations except for Chicot (2017-2018) and NEC (2016 only).

TABLE 10

Average milling yields of CLM04 and check varieties in Arkansas Rice Performance Trial (ARPT) conducted at six Arkansas locations, 2016-2018. (Dr. Jarrod Hardke, personal communication, 2018).

| Variety | Milling yields (% head rice-% total rice) | | | | | | |
|---|---|---|---|---|---|---|---|
| | Chicot† | Clay | NEC | NEREC | PTRS | RREC | Mean |
| CLM04 | 50-68 | 54-67 | 51-68 | 61-66 | 54-64 | 60-69 | 60-68 |
| CL272 | 33-66 | 56-68 | 48-68 | 61-69 | 46-66 | 58-70 | 57-69 |
| Jupiter | 53-68 | 61-69 | 55-69 | 60-67 | 53-65 | 60-69 | 60-68 |
| Titan | 33-67 | 57-69 | 44-69 | 59-68 | 51-66 | 53-69 | 52-68 |

†Test location: Chicot = Chicot Co., AR., Clay = Clay Co., AR., NEC = Newport Extension Center near Newport, AR., NEREC = Northeast Research and Extension Center at Keiser, AR., PTRS = Pine Tree Research Station near Colt, AR., and RREC = Rice Research and Extension Center near Stuttgart, AR. During 2016-2018, trials were conducted at all locations except for Chicot (2017-2018) and NEC (2016 only).

TABLE 11

Overall agronomic characteristics, stalk strength, and test weight of CLM04 and check varieties in the Arkansas Rice Performance Trial (ARPT) at six Arkansas locations, 2016-2018. (Dr. Jarrod Hardke, personal communication, 2018).

| Variety | Days to 50% heading | Height (inch) | Lodging (%) | Stalk strength | Test weight |
|---|---|---|---|---|---|
| CLM04 | 88 | 40 | 6.3 | 1.3 | 38.2 |
| CL272 | 87 | 39 | 0.0 | 1.0 | 39.3 |
| Jupiter | 88 | 39 | 9.8 | 1.5 | 37.9 |
| Titan | 83 | 40 | 3.5 | 1.3 | 39.0 |

TABLE 12

Grain yield of CLM04 and check varieties in the Arkansas Rice Performance Trial (ARPT) at five Arkansas locations, 2018. (Dr. Jarrod Hardke, personal communication, 2018).

| Variety | Grain yield (bushels/acre at 12% H$_2$O) | | | | | |
|---|---|---|---|---|---|---|
| | Chicot† | Clay | NEREC | PTRS | RREC | Mean |
| CLM04 | 211 | 226 | 180 | 209 | 196 | 205 |
| CL272 | 179 | 205 | 155 | 201 | 174 | 183 |
| Jupiter | 192 | 230 | 191 | 177 | 207 | 199 |
| Titan | 177 | 216 | 160 | 201 | 208 | 192 |

†Test location: Chicot = Chicot Co., AR., Clay = Clay Co., AR., NEREC = Keiser, AR., PTRS = Colt, AR., and RREC = Stuttgart, AR.

TABLE 13

Grain yield of CLM04 and check varieties in the Arkansas Rice Performance Trial (ARPT) conducted at five Arkansas locations, 2017. (Dr. Jarrod Hardke, personal communication, 2017).

| Variety | Grain yield (bushels/acre at 12% H$_2$O) | | | | | |
|---|---|---|---|---|---|---|
| | Chicot† | Clay | NEREC | PTRS | RREC | Mean |
| CLM04 | 205 | 205 | 206 | 204 | 191 | 202 |
| CL272 | 195 | 218 | 181 | 174 | 196 | 193 |
| Jupiter | 208 | 218 | 210 | 184 | 198 | 203 |
| Titan | 212 | 198 | 214 | 164 | 214 | 200 |

†Test location: Chicot = Chicot Co., AR., Clay = Clay Co., AR., NEREC = Northeast Research and Extension Center at Keiser, AR., PTRS = Pine Tree Research Station near Colt, AR., and RREC = Rice Research and Extension Center near Stuttgart, AR.

TABLE 14

Milling yields of CLM04 and check varieties in the Arkansas Rice Performance Trial (ARPT) conducted at five Arkansas locations, 2017. (Dr. Jarrod Hardke, personal communication, 2017).

| Variety | Milling yields (% head rice-% total rice) | | | | | |
|---|---|---|---|---|---|---|
| | Chicot† | Clay | NEREC | PTRS | RREC | Mean |
| CLM04 | 50-68 | 62-71 | 62-68 | 55-66 | 63-66 | 58-68 |
| CL272 | 33-67 | 61-71 | 61-69 | 43-65 | 64-68 | 52-68 |
| Jupiter | 54-68 | 61-70 | 64-68 | 55-65 | 62-65 | 59-67 |
| Titan | 33-68 | 49-69 | 60-69 | 50-66 | 61-67 | 51-68 |

†Test location: Chicot = Chicot Co., AR., Clay = Clay Co., AR., NEREC = Northeast Research and Extension Center at Keiser, AR., PTRS = Pine Tree Research Station near Colt, AR., and RREC = Rice Research and Extension Center near Stuttgart, AR.

TABLE 15

Average agronomical characteristics, stalk strength, and test weight of CLM04 and check varieties in the Arkansas Rice Performance Trial (ARPT) across five Arkansas locations, 2017. (Dr. Jarrod Hardke, personal communication, 2017).

| Variety | Days to 50% heading | Height (inch) | Lodging (%) | Stalk strength | Test weight |
|---|---|---|---|---|---|
| CLM04 | 90 | 37.4 | 0.0 | 1.0 | 38.3 |
| CL272 | 89 | 36.0 | 0.0 | 1.0 | 39.2 |
| Jupiter | 91 | 35.2 | 0.0 | 1.0 | 38.2 |
| Titan | 85 | 36.3 | 0.5 | 1.2 | 39.1 |

TABLE 16

Grain yield of CLM04 and check varieties in the Arkansas Rice Performance Trial (ARPT) conducted at five Arkansas locations, 2016. (Dr. Jarrod Hardke, personal communication, 2016).

| Variety | Gram yield (bushels/acre at 12% H$_2$O) | | | | | |
|---|---|---|---|---|---|---|
| | Clay† | NEC | NEREC | PTRS | RREC | Mean |
| CLM04 | 153 | 135 | 191 | 176 | 191 | 169 |
| CL272 | 198 | 152 | 188 | 178 | 162 | 176 |
| Jupiter | 133 | 132 | 207 | 157 | 207 | 167 |
| Titan | 209 | 155 | 201 | 170 | 223 | 192 |

†Test location: Clay = Clay Co., AR., NEC = Newport Extension Center near Newport, AR., NEREC = Northeast Research and Extension Center at Keiser, AR., PTRS = Pine Tree Research Station near Colt, AR., and RREC = Rice Research and Extension Center near Stuttgart, AR.

TABLE 17

Milling yields of CLM04 and check varieties in the Arkansas Rice Performance Trial (ARPT) conducted at five Arkansas locations, 2016. (Dr. Jarrod Hardke, personal communication, 2016).

| | Milling yields (% head rice-% total rice) | | | | | |
|---|---|---|---|---|---|---|
| Variety | Clay† | NEC | NEREC | PTRS | RREC | Mean |
| CLM04 | 55-67 | 58-69 | 61-69 | 54-64 | 59-68 | 57-67 |
| CL272 | 52-68 | 48-68 | 58-70 | 50-67 | 56-69 | 53-68 |
| Jupiter | 58-70 | 55-69 | 59-70 | 52-65 | 59-69 | 56-69 |
| Titan | 55-69 | 44-69 | 59-70 | 53-66 | 58-70 | 54-69 |

†Test location: Clay = Clay Co., AR., NEC = Newport Extension Center near Newport, AR., NEREC = Northeast Research and Extension Center at Keiser, AR., PTRS = Pine Tree Research Station near Colt, AR., and RREC = Rice Research and Extension Center near Stuttgart, AR.

TABLE 18

Average agronomical characteristics, stalk strength, and test weight of CLM04 and check varieties in the Arkansas Rice Performance Trial (ARPT) at five Arkansas locations, 2016. (Dr. Jarrod Hardke, personal communication, 2016).

| Variety | Days to 50% heading | Height (inch) | Lodging (%) | Stalk strength | Test weight |
|---|---|---|---|---|---|
| CLM04 | 87 | 41 | 12.5 | 1.6 | 38.2 |
| CL272 | 85 | 40 | 0.0 | 1.0 | 39.3 |
| Jupiter | 86 | 41 | 17.0 | 2.0 | 38.7 |
| Titan | 80 | 40 | 6.5 | 1.4 | 38.9 |

TABLE 19

Preliminary yield data of CLM04 and check varieties in the Producer Rice Evaluation Program (PREP) trials conducted at 10 locations across rice growing area of Arkansas, 2018. (Dr. Jarrod Hardke, personal communication, 2018).

| | Grain yield (bushels/acre at 12% H$_2$O) | | | | | | | | | | |
|---|---|---|---|---|---|---|---|---|---|---|---|
| Variety | CRA† | CRI | LON | PER | POI | PRA | RAN | STF | WHI | WOO | Mean |
| CLM04 | 234 | 227 | 203 | 210 | 151 | 200 | 201 | 202 | 220 | 205 | 205 |
| CL272 | 223 | 225 | 187 | 204 | 161 | 174 | 187 | 180 | 194 | 208 | 194 |
| Jupiter | 181 | 238 | 193 | 232 | 155 | 183 | 193 | 176 | 228 | 222 | 200 |
| Titan | 228 | 230 | 194 | 223 | 170 | 216 | 203 | 184 | 237 | 228 | 211 |

†Test location: CRA = Craighead Co., CRI = Crittenden Co., LON = Lonoke Co., PER = Perry Co., POI = Poinsett Co., PRA = Prairie Co., RAN = Randolph Co., STF = St. Francis Co., WHI = White Co., and WOO = Woodruff Co.

TABLE 20

Average yield, milling, and agronomical characteristics of CLM04 and check varieties in the Uniform Regional Rice Nursery (URRN) tested in Stuttgart, AR, Crowley, LA, Stoneville, MS, Malden, MO, and Beaumont, TX, 2016- 2018. Only nurseries with complete datasets were included.

| Variety | Days to 50% heading | Height (cm) | Lodging (%) | Yield (bu/A) | Yield (lb/A) | Head rice (%) | Total rice (%) |
|---|---|---|---|---|---|---|---|
| 2016-2018 Average | | | | | | | |
| CLM04 | 86 | 108 | 0 | 200 | 9,008 | 63.3 | 68.4 |
| CL272 | 84 | 101 | 0 | 189 | 8,491 | 59.8 | 68.9 |
| Jupiter | 85 | 97 | 0 | 192 | 8,631 | 62.6 | 67.7 |
| Titan | 80 | 98 | 0 | 196 | 8,828 | 62.3 | 69.0 |
| 2016 | | | | | | | |
| CLM04 | 85 | 107 | 0 | 185 | 8,317 | 61.5 | 67.3 |
| CL272 | 82 | 100 | 0 | 167 | 7,497 | 59.9 | 68.1 |
| Jupiter | 85 | 96 | 0 | 180 | 8,089 | 64.2 | 68.4 |
| Titan | 80 | 97 | 0 | 180 | 8,118 | 63.1 | 68.9 |
| 2017 | | | | | | | |
| CLM04 | 88 | 107 | 0 | 201 | 9,050 | 65.6 | 70.3 |
| CL272 | 87 | 101 | 0 | 203 | 9,121 | 61.0 | 69.6 |
| Jupiter | 88 | 97 | 0 | 201 | 9,067 | 60.6 | 68.0 |
| Titan | 82 | 100 | 0 | 219 | 9,833 | 60.7 | 69.2 |
| 2018 | | | | | | | |
| CLM04 | 84 | 109 | 0 | 220 | 9,887 | 63.6 | 67.6 |
| CL272 | 84 | 101 | 0 | 204 | 9,186 | 57.6 | 69.4 |
| Jupiter | 83 | 99 | 0 | 198 | 8,919 | 62.5 | 65.9 |
| Titan | 79 | 96 | 0 | 195 | 8,771 | 63.0 | 68.8 |

TABLE 21

Performance of CLM04 and check varieties in the Medium-grain Producer Rice Evaluation Program (PREP-MG) trials conducted at two locations in northeast Arkansas, 2017-2018. (Dr. Jarrod Hardke, personal communication, 2018).

| Variety | Yield (bu/A) | Lodging (%) | Head rice (%) | Total rice (%) |
|---|---|---|---|---|
| 2017-2018 Average | | | | |
| CLM04 | 185 | 6.3 | 51.1 | 69.5 |
| CL272 | 172 | 0.0 | 52.5 | 69.6 |
| Jupiter | 194 | 11.3 | 55.1 | 69.9 |
| Titan | 189 | 12.0 | 53.5 | 70.4 |
| 2017 | | | | |
| CLM04 | 202 | 0.0 | 51.1 | 69.5 |
| CL272 | 180 | 0.0 | 52.5 | 69.6 |
| Jupiter | 213 | 0.0 | 55.1 | 69.9 |
| Titan | 209 | 0.0 | 53.5 | 70.4 |
| 2018 | | | | |
| CLM04 | 169 | 12.5 | | |
| CL272 | 164 | 0.0 | | |
| Jupiter | 175 | 22.5 | | |
| Titan | 170 | 24.0 | | |

TABLE 22

Performance of CLM04 and check varieties in the Clearfield Advanced Yield Trial treated with 2x NewPath herbicide, Stuttgart, AR, 2018.

| Variety | Days to 50% heading | Height (cm) | Yield (bu/A) | Yield (lb/A) | Head rice (%) | Total rice (%) |
|---|---|---|---|---|---|---|
| CLM04 | 79 | 43 | 190 | 8,532 | 65.3 | 68.9 |
| CL272 | 80 | 44 | 171 | 7,700 | 61.8 | 66.7 |

TABLE 23

Performance of CLM04 and check varieties in Advanced/Elite Line Yield Trial (AYT) conducted at Northeast Research and Extension Center (NEREC), Pine Tree Research Station (PTRS), and Rice Research and Extension Center (RREC), 2017-2018.

| Variety | Days to 50% heading | Height (inch) | Lodging (%) | Yield (bu/A) | Yield (lb/A) | Head rice (%) | Total rice (%) |
|---|---|---|---|---|---|---|---|
| 3-Location Average | | | | | | | |
| CLM04 | 83 | 43 | 0 | 196 | 8,810 | 66.1 | 68.2 |
| CL272 | 83 | 41 | 0 | 187 | 8,413 | 67.8 | 69.1 |
| Jupiter | 83 | 38 | 0 | 198 | 8,929 | 67.7 | 69.2 |
| Titan | 77 | 41 | 0 | 204 | 9,161 | 69.8 | 71.1 |
| RREC | | | | | | | |
| CLM04 | 84 | 43 | 0 | 181 | 8,123 | 65.3 | 67.7 |
| CL272 | 84 | 41 | 0 | 173 | 7,763 | 68.3 | 70.0 |
| Jupiter | 85 | 38 | 0 | 190 | 8,567 | 68.6 | 70.0 |
| Titan | 79 | 42 | 0 | 208 | 9,362 | 70.4 | 72.0 |
| PTRS | | | | | | | |
| CLM04 | 77 | 41 | 0 | 204 | 9,160 | 66.8 | 68.7 |
| CL272 | 77 | 39 | 0 | 205 | 9,232 | 67.3 | 68.3 |
| Jupiter | 77 | 35 | 0 | 195 | 8,772 | 66.7 | 68.3 |
| Titan | 72 | 39 | 0 | 199 | 8,937 | 69.1 | 70.1 |
| NEREC | | | | | | | |
| CLM04 | 88 | 42 | 0 | 219 | 9,835 | | |
| CL272 | 86 | 40 | 0 | 198 | 8,894 | | |
| Jupiter | 86 | 40 | 0 | 218 | 9,811 | | |
| Titan | 78 | 40 | 0 | 200 | 8,984 | | |

TABLE 24

Influence of nitrogen (N) fertilizer rate on the grain yield of RU601030 rice, 2018 (Sunny Bottoms, personal communication, 2018).

| N Fertilizer Rate (lbs N/A) | Grain Yield LSU$^a$ (bushels/acre) |
|---|---|
| 0 | 97 |
| 30 | 145 |
| 60 | 179 |
| 90 | 209 |
| 120 | 234 |
| 150 | 240 |
| 180 | 242 |
| 210 | 230 |
| LSD$_{(\alpha=0.05)}$$^b$ | 22.7 |
| C.V. (%) | 7.78 |

$^a$Louisiana State University Agricultural Center's Rice Research Station near Crowley, LA.
$^b$LSD = least significant difference, C.V. = coefficient of variation.

TABLE 25

Development History - CLM04

| Year | Generation | Designation | Trials | Comments |
|---|---|---|---|---|
| 2013 | Cross | 13CRS187 | | Spring 2013 |
| 2013 | F1 | 13TP579 | Transplant | |
| 2013-14 | F2 | 13X4401-433 | F$_2$ Population | Puerto Rico |
| 2014 | F3 | 14P54617 | Progeny Row, Bulk | |
| 2015 | F4 | 15CSIT474 | Stuttgart Initial Trials - Clearfield (CSIT) | |
| 2016 | F5 | CLM04 | Uniform Regional Rice Nursery (URRN) | |
| 2016 | F5 | 16ARPT E259 | Arkansas Rice Performance Trial (ARPT) | |
| 2016-17† | F6 | CLM04 | Seed Increase/Purification | Puerto Rico |
| 2017 | F6 | 17AYT010 | Advanced/Elite Line Yield Trial (AYT) | |
| 2017 | F6 | 17ARPT E259 | ARPT | |
| 2017 | F6 | CLM04 | URRN | |
| 2017 | F6 | 17PREPMG E09 | Medium-grain Producer Rice Evaluation Program (PREP-MG) | |
| 2017 | F7 | CLM04 | Breeder Head Row Increase | |
| 2018 | F8 | 18AYT39 | AYT | |
| 2018 | F8 | 18ARPT E225 | ARPT | |
| 2018 | F8 | CLM04 | URRN | |
| 2018 | F8 | 18PREP | Producer Rice Evaluation Program (PREP) | |
| 2018 | F8 | 18PREPMG E10 | PREP-MG | |
| 2018 | F8 | 18CL EX624 | Clearfield Advanced Yield Trial | |
| 2018 | F8 | CLM04 | Foundation Seed Production | |

†Head rows purified off-season in Puerto Rico were used to grow breeder headrows in Stuttgart, AR, in summer 2017, and the resulting seeds were used for all 2018 small-plot and strip trials across Mid-South and Gulf Coast rice growing regions, as well as for growing foundation seed.

Herbicide Resistance of Rice Cultivar CLM04

Clearfield® (CL) rice is resistant to imidazolinone herbicides (WSSA Group 2), which control weeds by inhibiting the enzyme acetohydroxyacid synthase (AHAS), also called acetolactate synthase (ALS). CL rice was developed through mutagenesis of the ALS locus using traditional breeding techniques and is not considered genetically modified. The herbicide-resistance trait of this rice makes it particularly useful in regions where there is a need to control weedy rice and other tough grasses. Thus, the majority of rice cultivars planted in the southern United States are CL inbred or hybrid.

Accordingly, the present invention also provides rice seeds treated with an AHAS-inhibiting herbicide. AHAS-inhibiting herbicides include, without limitiation, imidazolinone herbicide, a sulfonylurea herbicide, a triazolopyrimidine herbicide, a pyrimidinyloxybenzoate herbicide, a sulfonylamino-carbonyltriazolinone herbicide, and a mixture thereof. However, in preferred embodiments, the AHAS-inhibiting herbicide is an imidazolinone herbicide or a mixture of two or more imidazolinone herbicides. Suitable imidazolinone herbicides include, without limitation, PURSUIT (imazethapyr), CADRE (imazapic), RAPTOR (imazamox), SCEPTER (imazaquin), ASSERT (imazethabenz), ARSENAL (imazapyr), a derivative of any of the aforementioned herbicides, and a mixture of two or more of the aforementioned herbicides, for example, imazapyr/imazamox (ODYSSEY). More specifically, the imidazolinone herbicide can be selected from, but is not limited to, 2-(4-isopropyl-4-methyl-5-oxo-2-imidiazolin-2-yl)-nicotinic acid, [2-(4-isopropyl)-4-][methyl-5-oxo-2-imidazolin-2-yl)-3-quinolinecarboxylic]acid, [5-ethyl-2-(4-isopropyl-]4-methyl-5-oxo-2-imidazolin-2-yl)-nicotinic acid, 2-(4-isopropyl-4-methyl-5-oxo-2-imidazolin-2-yl)-5-(methoxymethyl)-nicotinic acid, [2-(4-isopropyl-4-methyl-5-oxo-2-]imidazolin-2-yl)-5-methylnicotinic acid, and a mixture of methyl[6-(4-isopropyl-4-]methyl-5-oxo-2-imidazolin-2-yl)-m-toluate and methyl[2-(4-isopropyl-4-methyl-5-]oxo-2-imidazolin-2-yl)-p-toluate.

A wide variety of formulations can be employed for protecting plants from weeds, so as to enhance plant growth and reduce competition for nutrients. Customary formulations include, for example solutions, emulsions, suspensions, dusts, powders, pastes and granules. The use form depends on the particular intended purpose; in each case, it should ensure a fine and even distribution of the compound according to the invention.

The herbicide may be applied at pre-emergence, post-emergence, pre-planting or at planting to control weeds in areas surrounding the rice plants described herein. The herbicide and herbicide formulations can be applied in accordance with conventional methods, for example, by spraying, irrigation, dusting, or the like.

An herbicide can be used by itself or an herbicide formulation can be used that contains other additives. The herbicide can also be used as a seed treatment. Additives that may be found in an herbicide formulation include other herbicides, detergents, adjuvants, spreading agents, sticking agents, stabilizing agents, or the like. The herbicide formulation can be a wet or dry preparation and can include, but is not limited to, flowable powders, emulsifiable concentrates and liquid concentrates. Such formulations are prepared in a known manner, for example by extending the active compound with auxiliaries suitable for the formulation of agrochemicals, such as solvents and/or carriers, emulsifiers, surfactants and dispersants, preservatives, anti-foaming agents, anti-freezing agents, and also optionally colorants and/or binders and/or gelling agents.

Methods

This present invention provides methods for producing rice plants. In some embodiments, these methods involve planting a plurality of the rice seeds provided herein under conditions favorable for the growth of rice plants.

The plants of rice cultivar CLM04 have increased resistance to AHAS-inhibiting herbicides, particularly imidazolinone herbicides, and thus find use in methods for controlling weeds. Accordingly, the present invention provides methods for combating undesired vegetation. The methods involve contacting the rice seeds provided herein with an AHAS-inhibiting herbicide. The term "contacting" signifies that the active ingredient of the herbicide is on the surface of the seed at the time of application, though a greater or lesser amount of the ingredient may penetrate into the seed, depending on the method of application. The AHAS-inhibiting herbicide may be selected from the group consisting of an imidazolinone herbicide, a sulfonylurea herbicide, a triazolopyrimidine herbicide, a pyrimidinyloxybenzoate herbicide, a sulfonylamino-carbonyltriazolinone herbicide, or a mixture thereof. However, in preferred embodiments, the AHAS-inhibiting herbicide is an imidazolinone herbicide or a mixture of two or more imidazolinone herbicides.

The rice seeds may be contacted with the herbicide using any application method known in the art including, but not limited to, seed treatment, soil treatment, and foliar treatment. However, in preferred embodiments, the herbicide is applied to the seeds. Suitable seed treatment techniques include, without limitation, seed dressing, seed coating, seed dusting, seed soaking, and seed pelleting. In some embodiments, the herbicide is applied to the seeds before sowing and/or after pregermination. Pregermination refers to a process in which seeds are sprouted in the absence of soil. Thus, the phrase "after pregermination" refers to the period of development after germination has occurred (i.e., the root penetrates through the seed coat).

For the methods of the present invention, the preferred amount or concentration of the herbicide is an "effective amount" or "effective concentration, i.e., an amount or concentration that is sufficient to kill or inhibit the growth of a similar, wild-type, rice plant, rice plant tissue, rice plant cell, or rice seed, but that said amount does not kill or inhibit as severely the growth of the herbicide-resistant plants, plant tissues, plant cells, and seeds of the present invention. Typically, the effective amount of an herbicide is an amount that is routinely used in agricultural production systems to kill weeds of interest. Such an amount is known to those of ordinary skill in the art. Herbicide application rates generally range from 0.1 g to 10 kg of the active ingredient per 100 kg of seed, preferably from 1 g to 5 kg per 100 kg of seed, in particular from 1 g to 2.5 kg per 100 kg of seed.

The phrase "control of undesired vegetation" refers to the killing of weeds and/or otherwise retarding or inhibiting the normal growth of the weeds. Weeds, in the broadest sense, are understood as meaning all those plants which grow in locations where they are undesired. The weeds may include, for example, dicotyledonous and monocotyledonous weeds. Dicotyledonous weeds include, but are not limited to, weeds of the genera: *Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus*, and *Taraxacum*. Monocotyledonous weeds include, but are not limited to, weeds of the genera: *Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristyslis, Sagittaria, Eleocharis, Scirpus, Paspalum, Ischaemum, Sphenoclea, Dactyloctenium, Agrostis, Alopecurus*, and *Apera*. In addition, the weeds of the present invention can include crop plants that are growing in an undesired location. For example, a volunteer soybean plant that is in a field that predominantly comprises rice plants can be considered a weed, if the soybean plant is undesired in the field of rice plants. Another example of a weed of the present invention is red rice which is the same species as cultivated rice.

This present invention also provides methods for producing an herbicide-resistant rice plant. The methods involve crossing a first parent rice plant of cultivar CLM04 with a second parent rice plant that is not resistant to an herbicide. In some embodiments, a breeding cross is made to introduce new genetics into the CLM04 progeny (as opposed to a self or a sib cross, made to select among existing genetic alleles). In these embodiments, a population of hybrid rice plants will be produced that, on average, derive 50% of their alleles from cultivar CLM04. The resulting first generation (F1) hybrid rice seeds may be harvested and used to grow plants that express a subset of characteristics from CLM04. Alternatively, a plant of this population may be selected and repeatedly selfed or sibbed with a rice cultivar resulting from successive filial generations. In other embodiments, both the first and second parent rice plants can come from the rice cultivar CLM04. However, advantageously, the rice cultivar is used in crosses with other, different, rice cultivars to produce F1 rice seeds and plants with superior characteristics. In some embodiments, the rice cultivar CLM04 is crossed with a second rice plant that is transgenic. Rice cultivar CLM04 may also be crossed with other species, including those of the family Graminaceae, and especially of the genera *Zea, Tripsacum, Croix, Schlerachne, Polytoca, Chionachne*, and *Trilobachne*, of the tribe Maydeae. See the section below titled "Breeding Methods" for a detailed description of breeding techniques that may utilized with the present invention.

In some embodiments, a CLM04 progeny plant is selected that has molecular markers, morphological characteristics, and/or physiological characteristics in common with CLM04 (e.g., those listed in Table 1 and Table 2). Techniques such as RFLP-enhanced selection, genetic marker enhanced selection (e.g., SSR markers), and the making of double haploids may be utilized to identify progeny that share particular traits with CLM04.

Further, this invention provides methods for introducing a desired trait into rice cultivar CLM04. This may be accomplished using traditional breeding methods, such as back-crossing. Here, rice cultivar CLM04 is crossed with a second rice line expressing the desired trait and progeny with both the desired trait and characteristics of CLM04 are selected and crossed. These steps are repeated until plants with both the desired trait and essentially all the physiological and morphological characteristics of CLM04 have been produced.

Alternatively, the desired trait may be introduced by transforming the rice cultivar with a transgene. The transgene may confer at least one trait selected from the following: herbicide resistance; insect resistance; resistance to bacterial, fungal, or viral disease; modified fatty acid metabolism; modified carbohydrate metabolism; and male sterility. See the section below titled "Transformation Methods" for a detailed description of transformation techniques that may utilized with the present invention. The transgenic cultivar produced by these methods may be crossed with another cultivar to produce a new transgenic cultivar. Alternatively, the transgene incorporated by these methods could be moved into another cultivar using traditional backcrossing techniques.

Optionally, any of the disclosed methods may further comprise additional steps involving producing rice seed from the resulting rice plants and/or planting the rice seed.

The present invention encompasses all plants, or parts thereof, produced by the methods described herein, as well as the seeds produced by these plants. Further, any plants derived from rice cultivar CLM04 or produced from a cross using cultivar CLM04 are provided. This includes genetic variants, created either through traditional breeding methods or through transformation, as well as plants produced in a male-sterile form. Notably, this includes gene-converted plants, including those developed by backcrossing. Any of the seeds, plants, or plant parts provided may be utilized for human food, livestock feed, and as a raw material in industry.

The present invention also encompasses progeny of rice cultivar CLM04 comprising a combination of at least two CLM04 traits selected from those listed in the Tables and Detailed Description of the Invention, wherein the progeny rice plant is not significantly different from CLM04 for said traits, as determined at the 5% significance level when grown in the same environment. One of skill in the art knows how to compare a trait between two plant varieties to determine if there is a significant difference between them (Fehr and Walt, Principles of Cultivar Development, pp. 261-286 (1987)). Molecular markers or mean trait values may be used to identify a plant as progeny of CLM04. Alternatively, progeny may be identified through their filial relationship with rice cultivar CLM04 (e.g., as being within a certain number of breeding crosses of rice cultivar CLM04). For example, progeny produced by the methods described herein may be within 1, 2, 3, 4, or 5 breeding crosses of rice cultivar CLM04.

Tissue Culture

The present invention provides tissue cultures of regenerable cells or protoplasts produced from rice cultivar CLM04. As is well known in the art, tissue culture of rice can be used for the in vitro regeneration of a rice plant. Thus, such cells and protoplasts may be used to produce plants having the physiological and morphological characteristics of rice variety CLM04. The rice plants regenerated by these methods are also encompassed by the present invention.

As used herein, the term "tissue culture" describes a composition comprising isolated cells or a collection of such cells organized into parts of a plant. Exemplary tissues for culture include protoplasts, calli, plant clumps, and plant cells that can be grown in culture, or parts of plants, such as embryos, pollen, flowers, seeds, pods, leaves, stems, roots, root tips, and anthers. Culture of various rice tissues and regeneration of plants therefrom is well known in the art.

Breeding Methods

The goal of rice breeding is to develop new, superior rice cultivars and hybrids. A superior cultivar is produced when a new combination of desirable traits is formed within a single plant variety. Desirable traits may include higher seed yield, resistance to diseases and insects, better stems and roots, tolerance to low temperatures, and better agronomic characteristics or grain quality.

The breeding methods used with the present invention may involve a single-seed descent procedure, in which one seed per plant is harvested and used to plant the next generation. Alternatively, the methods may utilize a multiple-seed procedure, in which one or more seeds harvested from each plant in a population is threshed together to form a bulk which is used to plant the next generation.

Use of rice cultivar CLM04 in any plant breeding method is encompassed by the present invention. The choice of a breeding or selection method will depend on several factors, including the mode of plant reproduction, the heritability of the trait(s) being improved, and the type of cultivar used commercially (e.g., F1 hybrid cultivar, pureline cultivar). Popular selection methods include pedigree selection, modified pedigree selection, mass selection, recurrent selection, backcrossing, or a combination thereof.

Pedigree selection is commonly used for the improvement of self-pollinating crops. Two parents are crossed to produce an F1 population. An F2 population is produced by selfing one or several F1's. Selection of the best individuals may begin in the F2 population; then, beginning in the F3 generation, the best individuals in the best families are selected. Replicative testing of families can begin in the F4 generation to make selection of traits with low heritability more effective. At an advanced stage of inbreeding (e.g., F6 or F7), the best lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population, which is often subjected to additional cycles of selection.

Backcrossing is commonly used to transfer genes for highly heritable traits into a desirable homozygous cultivar or inbred line. The term "backcrossing" refers to the repeated crossing of hybrid progeny back to one of the parental plants, referred to as the recurrent parent. The plant that serves as the source of the transferred trait is called the donor parent. After the initial cross, individuals possessing the transferred trait are selected and repeatedly crossed to the recurrent parent. The resulting plant is expected to have the attributes of the recurrent parent along with the trait transferred from the donor parent.

Transformation Methods

As is noted above, the present invention provides plants and seeds of rice cultivar CLM04 in which additional traits have been transferred. While such traits may be selected for using traditional breeding methods, they may also be introduced as transgenes. "Transgenes" include both foreign genes and additional or modified versions of native genes. Plants can be genetically engineered to have a wide variety of traits of agronomic interest including, without limitation, male sterility, waxy starch, herbicide resistance, resistance for bacterial, fungal, or viral disease, insect resistance, male fertility, enhanced nutritional quality, industrial usage, yield stability, and yield enhancement. Many examples of genes that confer such traits have been described in the literature and are well known in the art. For example, the transgene may confer resistance to an additional herbicide selected from the group consisting of: glyphosate, sulfonylurea, imidazolinone, dicamba, glufosinate, phenoxy proprionic acid, L-phosphinothricin, cyclohexone, cyclohexanedione, triazine, 2,4-Dichlorophenoxyacetic acid, hydroxyphenyl-pyruvate dioxygenase (HPPD) inhibitors, and benzonitrile.

Transgenes are typically introduced in the form of an expression vector. As used herein, an "expression vector" is DNA comprising a gene operatively linked to a regulatory element (e.g., a promoter). The expression vector may contain one or more such gene/regulatory element combinations. The expression vector may also include additional sequences, such as a signal sequence or a tag, that modify the protein produced by the transgene. The vector may be a plasmid, and can be used alone or in combination with other plasmids.

Expression vectors include at least one genetic marker operably linked to a regulatory element (e.g., a promoter) that allows transformed cells containing the vector to be recovered by selection. In some embodiments, negative selection (i.e., inhibiting growth of cells that do not contain the selectable marker gene) it utilized. Negative selection markers include, for example, genes that result in detoxification of a chemical agent (e.g., an antibiotic or an herbicide) and genes that result in insensitivity to an inhibitor. Exemplary negative selection genes include neomycin phosphotransferase II (nptII), hygromycin phosphotransferase, gentamycin acetyl transferase, streptomycin phosphotransferase, and aminoglycoside-3'-adenyl transferase. In other embodiments, positive selection (i.e., screening for the product encoded by a reporter gene) is utilized. Exemplary reporter genes include β-glucuronidase, β-galactosidase, luciferase, chloramphenicol acetyltransferase, and Green Fluorescent Protein (GFP).

Transgene expression is typically driven by operably linking the transgene to a promoter within the expression vector. However, other regulatory elements may also be used to drive expression, either alone or in combination with a promoter. As used herein, a "promoter" is a region of DNA upstream of a transcription start site that is involved in recognition and binding of RNA polymerase for transcription initiation. Any class of promoter may be selected to drive the expression of a transgene. For example, the promoter may be "tissue-specific", "cell type-specific", "inducible", or "constitutive". Those of skill in the art know how to select a suitable promoter based the particular circumstances and genetic engineering goals.

Methods for producing transgenic plants are well known in the art. General descriptions of plant expression vectors, reporter genes, and transformation protocols can be found in Gruber, et al., "Vectors for Plant Transformation", in *Methods in Plant Molecular Biology & Biotechnology* in Glich, et al., (Eds. pp. 89-119, CRC Press, 1993). General methods of culturing plant tissues are provided for example by Maki, et al., "Procedures for Introducing Foreign DNA into Plants" in *Methods in Plant Molecular Biology & Biotechnology*, Glich, et al., (Eds. pp. 67-88 CRC Press, 1993); and by Phillips, et al., "Cell-Tissue Culture and In-Vitro Manipulation" in *Corn & Corn Improvement*, 3rd Edition; Sprague, et al., (Eds. pp. 345-387 American Society of Agronomy Inc., 1988). Methods of introducing expression vectors into plant tissue include direct gene transfer methods, such as microprojectile-mediated delivery, DNA injection, and electroporation, as well as the direct infection or co-cultivation of plant cells with *Agrobacterium tumefaciens*, described for example by Horsch et al., *Science,* 227:1229 (1985). Descriptions of *Agrobacterium* vector systems and methods for *Agrobacterium*-mediated gene transfer are provided by Gruber, et al., supra.

REFERENCES

Linscombe, S. D., Jodari, F., McKenzie, K. S., Bollich, P. K., Groth, D. E., White, L. M., Dunand, R. T., Sanders, D. E. 1993. Registration of 'Bengal' rice. Crop Science 33:645-646.

Sha, X. Linscombe, S. D., Chu, Q., Groth, D. E., White, L. M., Bond, J., Dunand, R. T., and Utomo, H. 2006 Registration of 'Jupiter' rice. Crop Science 46:1811-1812.

Sha, X., Linscombe, S. D., Blanche, S. B., Groth, D. E., Harrell, D., White, L. M., and Theunissen, S. J. 2010. Registration of 'Neptune' southern medium-grain rice. Journal of Plant Registrations 4:179-182.

Sha, X., Linscombe, S. D., and Groth, D. E. 2007. Field evaluation of Imidazolinone-tolerant Clearfield rice (*Oryza sativa*) at nine Louisiana locations. Crop Science 47:1177-1185.

Deposit Information

A deposit of the University of Arkansas Division of Agriculture Rice Research and Extension Center proprietary rice cultivar CLM04 disclosed above and recited in the appended claims has been made with the American Type Culture Collection (ATCC), 10801 University Boulevard, Manassas, Va. 20110. The date of deposit was Jan. 14, 2020. The deposit of 2,500 seeds was taken from the same deposit maintained by the University of Arkansas Division of Agriculture Rice Research and Extension Center (2900 Hwy 130 E., Stuttgart, Ark. 72160) and BASF since prior to the filing date of this application. All restrictions will be irrevocably removed upon granting of a patent, and the deposit is intended to meet all of the requirements of 37 C.F.R. §§ 1.801-1.809. The ATCC Accession Number is PTA-126573. The deposit will be maintained in the depository for a period of thirty years, or five years after the last request, or for the enforceable life of the patent, whichever is longer, and will be replaced as necessary during that period.

What is claimed is:

1. A rice seed of the variety CLM04, a representative sample of seed of said variety having been deposited under ATCC Accession No. PTA-126573.

2. The rice seed of claim 1, wherein said seed is treated with an acetohydroxyacid synthase (AHAS)-inhibiting herbicide.

3. The rice seed of claim 2, wherein said AHAS-inhibiting herbicide is selected from the group consisting of imidazolinone herbicides, sulfonylurea herbicides, triazolopyrimidine herbicides, pyrimidinyloxybenzoate herbicides, sulfonylamino-carbonyltriazolinone herbicides, and mixtures thereof.

4. The rice seed of claim 2, wherein said AHAS-inhibiting herbicide is an imidazolinone herbicide or a mixture of two or more imidazolinone herbicides.

5. The rice seed of claim 4, wherein the imidazolinone herbicide is selected from the group consisting of imazapyr, imazapic, imazethapyr, imazamox, imazamethabenz, imazaquin herbicides, and mixtures thereof.

6. A rice plant, or a part thereof, produced by growing the seed of claim 1.

7. Pollen or an ovule of the plant of claim 6.

8. A method for producing rice plants, said method comprising planting a plurality of rice seeds as recited in claim 1 under conditions favorable for the growth of rice plants.

9. The method of claim 8, further comprising the step of producing rice seed from the resulting rice plants.

10. A rice seed produced by the method of claim 9.

11. A method for combating undesired vegetation comprising contacting the rice seed of claim 1, before sowing and/or after pregermination, with an AHAS-inhibiting herbicide.

12. The method of claim 11, wherein said AHAS-inhibiting herbicide is selected from the group consisting of imidazolinone herbicides, sulfonylurea herbicides, triazolopyrimidine herbicides, pyrimidinyloxybenzoate herbicides, sulfonylamino-carbonyltriazolinone herbicides, and mixtures thereof.

13. The method of claim 12, wherein said AHAS-inhibiting herbicide is an imidazolinone herbicide or a mixture of two or more imidazolinone herbicides.

14. A tissue culture of regenerable cells or protoplasts produced from the rice plant of claim 6.

15. The tissue culture of claim 14, wherein said cells or protoplasts are produced from a tissue selected from the group consisting of embryos, meristematic cells, pollen, leaves, anthers, roots, root tips, pistils, anthers, cotyledon, hypocotyl, panicles, flowers, seeds, and stems.

16. A rice plant regenerated from the tissue culture of claim 14, wherein the regenerated plant has all of the morphological and physiological characteristics of rice plant of line CLM04.

17. A method for producing an herbicide-resistant rice plant, said method comprising crossing a first parent rice plant with a second parent rice plant, wherein the first parent rice plant is the rice plant of claim 6, and wherein the second parent rice plant is not resistant to an herbicide.

18. The method of claim 17, further comprising selecting for a progeny rice plant that is resistant to at least one AHAS-inhibiting herbicide.

19. The method of claim 18, wherein said AHAS-inhibiting herbicide is an imidazolinone herbicide or a mixture of two or more imidazolinone herbicides.

20. An herbicide-resistant rice plant produced by the method of claim 17.

21. The method of claim 17, further comprising the step of producing rice seed from the resulting rice plants.

22. The method of claim 17, wherein the second parent rice plant is transgenic.

23. A method comprising transforming the rice plant of claim 6 with a transgene, wherein the transgene confers at least one trait selected from the group consisting of: herbicide resistance; insect resistance; resistance to bacterial, fungal, or viral disease; modified fatty acid metabolism; modified carbohydrate metabolism; and male sterility.

24. A rice plant or part thereof, or rice seed, produced by the method of claim 23.

25. A method of introducing a desired trait into rice cultivar CLM04, said method comprising the steps of:
    (a) crossing plants as recited in claim 6 with plants of another rice line expressing the desired trait, to produce progeny plants;
    (b) selecting progeny plants that express the desired trait, to produce selected progeny plants;
    (c) crossing the selected progeny plants with plants of rice cultivar CLM04 to produce new progeny plants;
    (d) selecting new progeny plants that express the desired trait; and
    (e) repeating steps (c) and (d) three or more times in succession, to produce selected higher generation backcross progeny plants that express the desired trait.

26. The method of claim 25, additionally comprising the step of planting a plurality of rice seed produced by selecting higher generation backcross progeny plants under conditions favorable for the growth of rice plants and optionally comprising the step of producing rice seed from the resulting rice plants.

27. A method for controlling weeds in the vicinity of a rice plant of rice cultivar CLM04, said method comprising applying an effective amount of at least one AHAS-inhibiting herbicide to the weeds and to the rice plant, a representative sample of seed of said variety having been deposited under ATCC Accession No. PTA-126573.

28. The method of claim 27, wherein said AHAS-inhibiting herbicide is selected from the group consisting of imidazolinone herbicides, sulfonylurea herbicides, triazolopyrimidine herbicides, pyrimidinyloxybenzoate herbicides, sulfonylamino-carbonyltriazolinone herbicides, and mixtures thereof.

29. The method of claim 28, wherein said AHAS-inhibiting herbicide is an imidazolinone herbicide or a mixture of two or more imidazolinone herbicides.

30. The method of claim 29, wherein said imidazolinone herbicide is selected from the group consisting of imazapyr, imazapic, imazethapyr, imazamox, imazamethabenz, imazaquin herbicides, and mixtures thereof.

\* \* \* \* \*